United States Patent [19]

Stönner et al.

[11] Patent Number: 5,382,717
[45] Date of Patent: Jan. 17, 1995

[54] PROCESS OF CONTROLLING THE RATE AT WHICH USED CATALYST IS RECYCLED TO HYDROGENATING MEANS FOR PREPARING FATTY ALCOHOLS FROM FATTY ACID DERIVATIVES

[75] Inventors: Hans-Martin Stönner, Eschborn; Henning Buchold, Hanau, both of Germany

[73] Assignee: Metallgesellschaft Aktiengesellschaft, Frankfurt am Main, Germany

[21] Appl. No.: 195,854

[22] Filed: Feb. 10, 1994

[30] Foreign Application Priority Data

Feb. 13, 1993 [DE] Germany ............... 4304420

[51] Int. Cl.$^6$ .............. C07C 29/149; C07C 31/125
[52] U.S. Cl. ............................................ 568/885
[58] Field of Search ................................. 568/885

[56] References Cited

U.S. PATENT DOCUMENTS

| | | | |
|---|---|---|---|
| 2,080,419 | 5/1937 | Green | 568/885 |
| 2,750,429 | 6/1956 | De Nora | |
| 3,180,898 | 4/1965 | Eisenlohr et al. | 568/885 |
| 4,259,536 | 3/1981 | Voeste | |
| 4,482,766 | 11/1984 | Stonner | |

FOREIGN PATENT DOCUMENTS 1112056 8/1961 Germany .
3221307 12/1985 Germany .
326946 2/1958 Switzerland .

*Primary Examiner*—Joseph E. Evans
*Attorney, Agent, or Firm*—Herbert Dubno

[57] ABSTRACT

Fatty acids and/or fatty acid derivatives as well as hydrogen, fresh catalyst and a dispersion which contains used catalyst are supplied to the hydrogenating means, which are operated at temperatures in the range from 100° to 400° C. and under pressures in the range from 20 to 400 bars to produce a product stream, which contains fatty alcohols and used catalyst. A part of the product stream is circulated. A first partial stream Is withdrawn at a controllable rate from the circulating stream and is passed through a separator. A product which is rich in fatty alcohol and a dispersion which contains used catalyst are separately delivered by the separator. The dispersion is recycled to the hydrogenating means. A second partial stream is withdrawn at a controllable rate from the circulating product stream. Used catalyst is separated from the second partial stream and is removed from the process. The rate at which used catalyst is fed to the hydrogenating means can be increased in that the rate of the second partial stream is decreased.

10 Claims, 1 Drawing Sheet

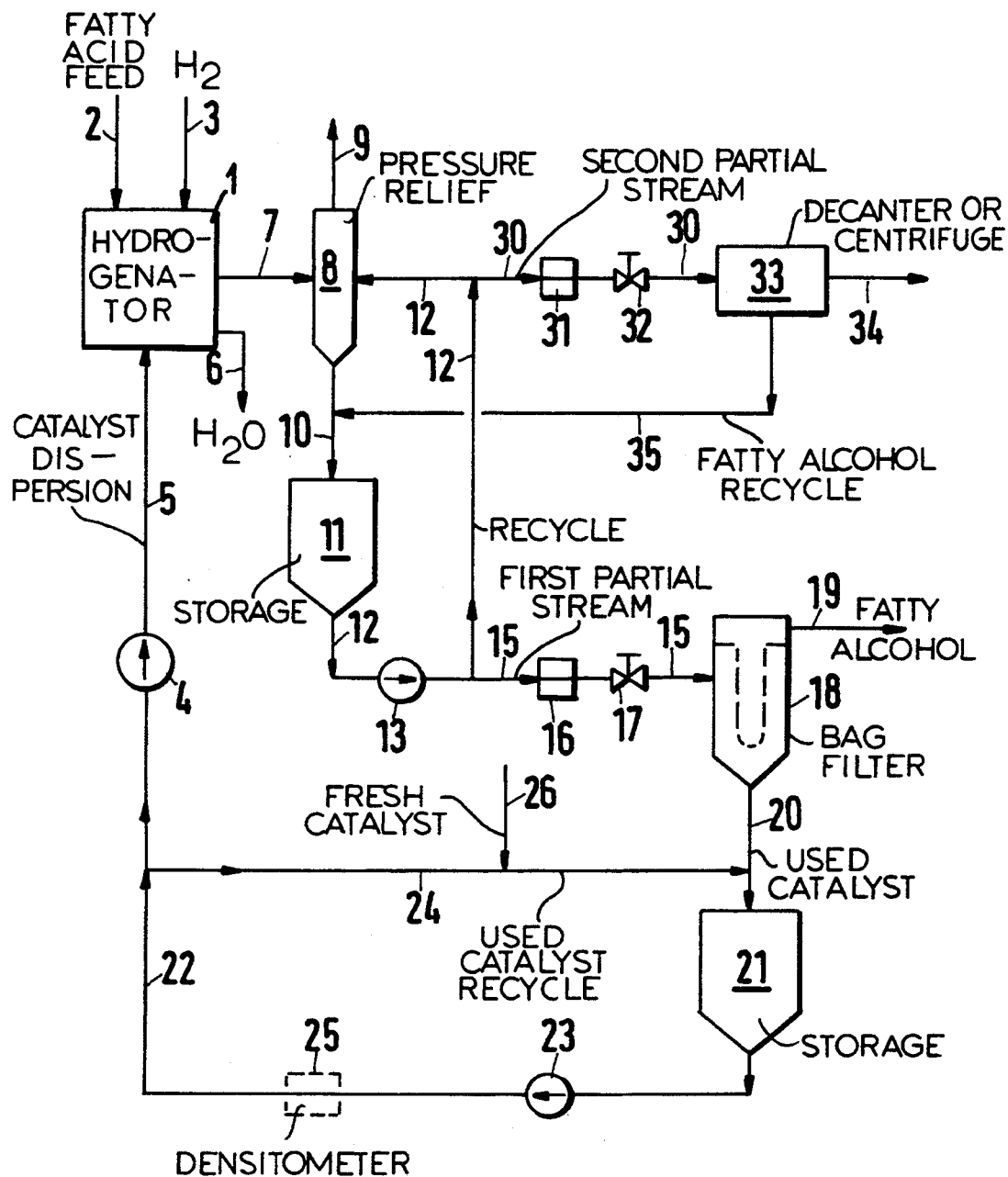

＝＝

PROCESS OF CONTROLLING THE RATE AT WHICH USED CATALYST IS RECYCLED TO HYDROGENATING MEANS FOR PREPARING FATTY ALCOHOLS FROM FATTY ACID DERIVATIVES

FIELD OF THE INVENTION

Our present invention relates to the catalyzed hydrogenation of fatty acids to fatty alcohols. More particularly, the invention relates to a process of controlling the rate at which used catalyst is recycled to a hydrogenator supplied with fatty acids and/or fatty acid derivatives as well as hydrogen, fresh catalyst, and a dispersion which contains used catalyst, to produce a product stream which contains fatty alcohols and used catalyst at a temperature in the range of 100° to 400° C. and under a pressure in the range from 20 to 400 bars.

BACKGROUND OF THE INVENTION

U.S. Pat. Nos. 2,750,429, 4,259,536 and 4,482,766 disclose the preparation of fatty alcohols by the hydrogenation of fatty acids and/or fatty acid derivatives. For that purpose a very finely divided metal catalyst, which can contain copper, and usually has a particle size in the range from 1 to 100 micrometers, is employed. The used catalyst is contained in the product stream which is rich in fatty alcohols. The used catalyst is separated from that product stream and is recycled at least in part to the hydrogenating stage. Derivatives which may be supplied to the hydrogenating stage instead of fatty acids can comprise fatty acid esters or glycerides.

OBJECT OF THE INVENTION

It is an object of the invention to provide an improved process and to control in a simple manner the rate at which used catalyst is recycled to the hydrogenating stage.

SUMMARY OF THE INVENTION

In accordance with the invention the product stream from the catalytic hydrogenation is circulated in part, a first partial stream at a controllable rate is withdrawn from the circulating stream and is passed through separating means, a product which is rich in fatty alcohols and a dispersion which contains used catalyst are separately withdrawn from the separating means, the dispersion is recycled to the hydrogenating means, a second partial stream is withdrawn at a controllable rate (volume per unit time) from the circulating stream, the used catalyst is separated from the second partial stream and is removed from the process, the rate at which used catalyst is supplied to the hydrogenating means is increased by decreasing the rate of the second partial stream and the rate at which used catalyst is supplied to the hydrogenating means is decreased by increasing the rate of the second partial stream. The separating means may consist of a backwashable filter or a high--performance centrifuge.

During normal operation the rates of the first and second partial streams are maintained constant and small fluctuations of the concentration of catalyst in the hydrogenating means will automatically be compensated because a decrease of the catalyst concentration will have the result that catalyst is removed from the process at a lower rate in the second partial stream and a rise of the catalyst concentration will have the result that more catalyst is withdrawn in the second partial stream. As a result, the concentration of catalyst will be automatically stabilized without the need for an additional supply of fresh catalyst.

The used catalyst is suitably separated from the second partial stream by centrifuging or decanting. This can desirably be effected without a supply of filtering aids and will result in the formation of a low-liquid phase, which contains 50 to 80% by weight solids. That phase, which contains the used catalysts, can readily be disposed of.

BRIEF DESCRIPTION OF THE DRAWING

The above and other objects, features, and advantages will become more readily apparent from the following description, reference being made to the accompanying drawing the sole FIGURE of which is a flow diagram illustrating the process of the invention.

SPECIFIC DESCRIPTION

Consisting of a mixture of fatty acids, the feedstock to be hydrogenated is supplied at a controlled rate to the hydrogenator 1 through line 2. Hydrogen is fed through line 3.

A dispersion which contains used catalyst is supplied through line 5 by a high-pressure metering pump 4. The product stream containing fatty alcohols and used catalyst is withdrawn in line 7 and is first fed to a pressure relief vessel 8. Reaction water which is formed is removed through line 6. Hydrogen-containing gas which has been flashed off is withdrawn in line 9.

The liquid product which has been relieved from pressure flows in line 10 to an interstage vessel 11. A part of the product stream is recycled in the circulating line 12 by the circulating pump 13 to the pressure relief vessel 8.

A first partial stream of the product stream in the circulating line 12 is withdrawn in line 15 and is passed through a flowmeter 16 and a flow control valve 17 and fed to the baa filter 18. A product which is rich in fatty alcohols and free of solids is recovered in the filter and withdrawn in line 19. That product can be purified to a high purity by means which are not shown.

A dispersion which contains used catalyst becomes available in the filter 18 and is first fed in line 20 to an interstage vessel 21 and is subsequently fed in part to line 5 through the line 22 by the backing pump 23 into the line 5. A part of the dispersion is desirably continuously recycled through line 24 to the interstage vessel 21.

Fresh catalyst from line 26 is admixed at a controlled rate to the dispersion in line 24 so that the fresh catalyst is homogeneously distributed in the dispersion.

A second partial stream of the liquid product is branched from the circulating line 12 through line 30 and is fed to a decanter 33 through a flowmeter 31 and a flow control valve 32. The decanter 33 may be replaced, e.g. by a centrifuge. The decanter 33 delivers in line 34 a phase which is rich in catalyst and usually contains 50 to 80% by weight solids. That phase can readily be disposed of. The fatty alcohol which is separated in the decanter 33 is admixed through line 35 to the product stream in line 10.

The product streams which are withdrawn from the circulating line 12 through lines 15 and 30 are variable and have different rates, the ratio of which is usually in the range from 100:1 to 5:1. When it is desired to increase the rate at which used catalyst is supplied to the hydrogenating means, the flow control valve 32 is actuated to decrease the rate at which the second partial stream is flowing in line 30. As a result, the rate at which catalyst is withdrawn through the line 34 is temporarily decreased so that the catalyst content in the dispersion flowing in lines 12, 15 and 20 is increased. As a result, the catalyst content is increased in line 22 and in line 5, in which the used catalyst together with fresh catalyst is supplied to the hydrogenating means 1. When a steady state has finally been reached, catalyst is withdrawn through line 34 at exactly the rate at which catalyst is supplied through line 26. To ensure that the dispersion in line 22 is pumpable, it may be desirable to provide a density meter, which is indicated by a broken line at 25.

Analogously, the rate at which used catalyst is supplied to the hydrogenating means 1 can be decreased by increasing the rate at which the second partial stream is withdrawn in line 30. This results in a temporary increase of the rate at which catalyst is withdrawn through line 34 and in a simultaneous decrease of the catalyst content in lines 12, 15 and 20. As a result, the catalyst content of the dispersion flowing in line 5 is decreased. During such control actions the rate at which fresh catalyst is supplied through line 26 need not be changed.

EXAMPLE

A plant as shown in the drawing comprises a hydrogenator 1 as disclosed in U.S. Pat. No. 4,259,536.

In that plant, raw fatty alcohol at a rate of 4081 kg/h is prepared from 4334 kg/h fatty acid, which has been derived from palm kernel oil is supplied in line 2.

The raw fatty alcohol is withdrawn in line 19. The fatty acid has substantially 12 to 18 carbon atoms per molecule and a saponification number of 252 mg KOH/g.

The hydrogenator 1 is fed with 87 kg/h fresh hydrogen in line 3. Hydrogen is circulated at a rate of 1653/h by means which are not shown. The hydrogenating reactor is operated under a pressure of 296 bars and at a temperature of 265° C.

A copper-containing catalyst powder is used which has a particle size from 1 to 50 micrometers and is commercially available from Süd-Chemie, Munich, Germany under the designation G00G-O. 3.1 catalyst per liter of fatty acid feedstock are continuously supplied through line 26 to the plant and catalyst is withdrawn at the same rate from the process in line 34. Further process data, some of which have been calculated, are apparent from the following column A of the following Table:

|  | A | B |
|---|---|---|
| Catalyst content in line 12 | 4 wt. % | 6 wt. % |
| Weight ratio of fresh catalyst to used datalyst in line 5 | 14.84 | 22.85 |
| Rate of product in line 30 | 420 l/h | 280 l/h |
| Saponification number of product in line 19, mg KOH/G | 5 | 5 |
| By-products, particularly hydrocarbons, in the product in line 19 | 0.30 wt. % | 0.22 wt. % |

Upon a decrease of the rate of product in line 30 to 280 l/h, the catalyst content in that line rises gradually from 4% by weight to 6% by weight, which rate is asymptotically reached after an operation for about 400 hours. During that time the hydrogenating reactor is operated under an unchanged pressure but the temperature therein is decreased in steps to 258° C. so that the saponification number of the raw fatty alcohol in line 19 remains constant. Further data relating to the new steady state which is reached are apparent from column B of the above Table.

In an inverse operation starting from the data in column B the rate of product in line 30 may be increased to 420 l/h so that the catalyst concentration of 4% by weight is asymptotically approached in line 30. In that case the temperature in the reactor is swiftly increased from 258° C. to 265° C. so that the saponification number in the raw fatty alcohol in line 19 does not rise above 5 mg KOH/g.

The above-mentioned data will be obtained if fresh catalyst is constantly supplied in line 26 at a rate of 3.1 g per liter of fatty acid feedstock in line 2. If that supply rate of fresh catalyst is doubled to 6.2 g/l, the rate at which product is withdrawn from line 30 must also be doubled if the concentration of catalyst in lines 12, 15 and 30 is to be returned to the original value after a certain operating time. It is apparent that the catalyst balance in the hydrogenating plant can be controlled by the process described in a simple manner without an occurrence of nonpermissible or undesired catalyst concentrations.

We claim:

1. A process for controlling a rate at which used catalyst is recycled to hydrogenation of a fatty acid component selected from the group which consists of at least one fatty acid, at least one fatty acid derivative and mixtures thereof, comprising the steps of:
    (a) deriving from the hydrogenation of said fatty acid component a product stream containing fatty alcohols and used catalyst and produced at a temperature in a range of 100° to 400° C. and a pressure in a range of 20 to 400 bars;
    (b) forming a circulating stream of at least part of said product stream;
    (c) withdrawing from the circulating stream at a controllable rate a first partial stream;
    (d) separating said first partial stream into a product rich in fatty alcohols and a dispersion containing used catalyst;
    (e) recycling said dispersion containing used catalyst to said hydrogenation;
    (f) withdrawing from the circulating stream a second partial stream;
    (g) removing used catalyst from the withdrawn second partial stream and from the process; and
    (h) increasing a rate at which used catalyst is supplied to the hydrogenation by decreasing the rate at which said second partial stream is withdrawn from said circulating stream, and decreasing the rate at which used catalyst is supplied to the hydrogenation by increasing the rate at which said second partial stream is withdrawn from said circulating stream.

2. The process defined in claim 1, further comprising adding fresh catalyst for said hydrogenation to said dispersion.

3. The process defined in claim 2 wherein a portion of said dispersion is recycled, said fresh catalyst being added to said recycled portion of said dispersion.

4. The process defined in claim 1 wherein said used catalyst is separated from said second partial stream by centrifugation.

5. The process defined in claim 1 wherein said used catalyst is separated from said second partial stream by decantation.

6. The process defined in claim 1, further comprising the steps of:

recovering following separation of used catalyst from said second partial stream a liquid stream; and admixing said liquid stream with said product stream.

7. The process defined in claim 6, further comprising adding fresh catalyst for said hydrogenation to said dispersion.

8. The process defined in claim 7 wherein a portion of said dispersion is recycled, said fresh catalyst being added to said recycled portion of said dispersion.

9. The process defined in claim 8 wherein said used catalyst is separated from said second partial stream by centrifugation.

10. The process defined in claim 8 wherein said used catalyst is separated from said second partial stream by decantation.

* * * * *